United States Patent [19]

Ryan et al.

[11] Patent Number: 5,216,160
[45] Date of Patent: Jun. 1, 1993

[54] PROCESS FOR THE PRODUCTION OF 4-AMINO-2-CHLORO-5-CYANO-6-(METHYLTHIO)PYRIMIDINE

[75] Inventors: Gary Ryan, Visp, Switzerland; Hans P. Mettler, Flemington, N.J.; Felix Previdoli, Brig, Switzerland

[73] Assignee: Lonza Ltd., Gampel/Valais, Switzerland

[21] Appl. No.: 865,251

[22] Filed: Apr. 8, 1992

[30] Foreign Application Priority Data

Apr. 11, 1991 [CH] Switzerland ............ 1085/91

[51] Int. Cl.$^5$ .......................... C07D 239/47
[52] U.S. Cl. ................................ 544/319
[58] Field of Search ......................... 544/319

[56] References Cited

FOREIGN PATENT DOCUMENTS 0244360 11/1987 European Pat. Off. .

OTHER PUBLICATIONS

Kristinsson, J. Chem., Soc. Commun., (1974), p. 350.
A. Hantzsch and M. Wolvekamp, Justus Liebigs Ann. Chem., vol. 331, (1904), pp. 265 to 297.
R. Gompper and W. Topfl, Chem. Ber., vol. 95, (1962), pp. 2861 to 2870.
H. Kristinsson, *Journal of the Chemical Society*, "Synthesis of 5-Cyanopyrimidines" (1974), p. 350.

*Primary Examiner*—John M. Ford
*Attorney, Agent, or Firm*—Fisher, Christen & Sabol

[57] ABSTRACT

4-Amino-2-chloro-5-cyano-6-(methylthio)primidine is produced from dicyanoketene dimethyl thioacetal and cyanamide by condensation in the presence of a base and subsequent cyclization in the presence of hydrochloric acid. The dicyanoketenedimeth thioacetal is available by reaction of malononitrile, with carbon disulfide and a base and subsequent methylation with dimethyl sulfate. The reaction sequence yields the pyrimidine derivative in good yield and practically free of by-products.

10 Claims, No Drawings

PROCESS FOR THE PRODUCTION OF 4-AMINO-2-CHLORO-5-CYANO-6-(METHYLTHIO)PYRIMIDINE

BACKGROUND OF THE INVENTION
1. Field Of The Invention

The invention relates to a process for the production of 4-amino-2-chloro-5-cyano-6-(methylthio)pyrimidine (I) of the formula:

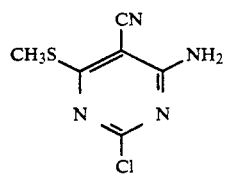

wherein 2-chloropyrimidines are intermediate products for the synthesis of 2-aminopyrimidines, a class of substances which contains numerous effective pesticides.

2. Background Art

An important representative of the 2-chloropyrimidines is 4-amino-2-chloro-5-cyano-6-(methylthio)-pyrimidine, whose methylthio group can be nucleophilically exchanged optionally after oxidation to the methanesulfonyl group [European Published Patent Application No. 0244360].

The known process for the production of 4-amino-2-chloro-5-cyano-6-(methylthio)pyrimidine [H. Kristinsson, J. Chem. Soc. Chem. Commun., (1974), page 350] starts from cyanamide and carbon disulfide, which with potassium hydroxide yield the dipotassium salt of cyanimidodithiocarbonic acid [A. Hantzsch and M. Wolvekamp, Justus Liebigs Ann. Chem., Vol. 331, (1904), page 282]. This is reacted with dimethyl sulfate to dimethyl cyanimidedithiocarbonate which adds malononitrile in the presence of sodium methylate. By adding hydrochloric acid the addition product is cyclized to the corresponding pyrimidine. In this way, not only the desired product results but also the isomeric 2-amino-4-chloro-5-cyano-6-(methylthio)pyrimidine, namely in the ratio of 3:2 (2-amino/4-amino-) so that with a total yield of 88 percent, the effective yield is only about 35 percent.

BROAD DESCRIPTION OF THE INVENTION

The main object of the invention is to provide a process which results in a high yield of 4-amino-2-chloro-5-cyano-6-(methylthio)pyrimidine and only small amounts of by-products. Other objects and advantages of the invention are set out herein or are obvious herefrom to one skilled in the art.

The objects and advantages of the invention are achieved by the process of the invention.

The invention involves a process for the production of 4-amino-2-chloro-5-cyano-6-(methylthio)pyrimidine of the formula:

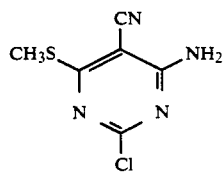

In a first step, malononitrile is reacted with carbon disulfide in the presence of a strong base to a dianion of dicyanodithioacetic acid of the formula:

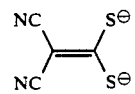

The latter then is methylated with a methylating agent to dicyanoketene dimethyl thioacetal of the formula:

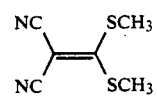

The latter is condensed with cyanamide in the presence of a base to the anion of 2-cyano-3-cyanamino-3-methylthio-acrylonitrile of the formula:

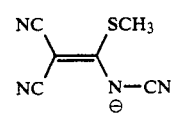

The latter is cyclized in the presence of hydrochloric acid to 4-amino-2-chloro-5-cyano-6-(methylthio)-pyrimidine.

Preferably an alkali alcoholate each is used as the base. Preferably in each case the corresponding alcohol is used as solvent in the reactions in the presence of alkali alcoholate. Preferably sodium ethylate is used as the alkali alcoholate. Preferably, in the reaction of malononitrile with the carbon disulfide, the malononitrile is introduced with an equivalent of base and the carbon disulfide is added synchronously with a second equivalent of base. Preferably dimethyl sulfate is used as the methylating agent. Preferably the hydrogen chloride is used as aqueous hydrochloric acid.

DETAILED DESCRIPTION OF THE INVENTION

It was found that surprisingly, 4-amino-2-chloro-5-cyano-6-(methylthio)pyrimidine can be obtained in a very good yield and practically free of by-products, by first reacting the malononitrile with carbon disulfide and an alkali-alcoholate to the corresponding dialkali salt of dicyanodithioacetic acid of the formula:

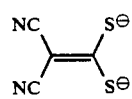

and then converting it with a methylating agent, for example, dimethyl sulfate, into the dicyanoketene dimethyl thioacetal of the formula:

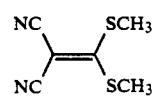

The latter is condensed with cyanamide in the presence of a base to the anion of the corresponding dicyanoketene S,N-acetal of the formula:

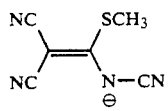

which is cyclized to the target compound analogously to the known process in the presence of hydrochloric acid.

The first part of the synthesis up to dicyanoketene dimethyl thioacetal is known in the art [R. Gompper and W. Töpfl, Chem. Ber., Vol. 95, (1962), pages 2861 to 2870]. The yield according to the literature (68 percent) can also be markedly increased, when first the anion is formed from the introduced malonitriles with an equivalent of base and the carbon disulfide is added simultaneously with the second equivalent of base instead of carbon disulfide and base being alternately added in portions.

As the base for the condensation of the dimethyl mercaptal with cyanamide, an alkali alcoholate is preferably used. Especially preferred are sodium alcoholates, especially sodium ethylate. However, other bases, for example, alkali hydroxides, can be used.

The condensation is performed suitably in a polar solvent, for example, in a lower alcohol. If an alcoholate is used as the base, the corresponding alcohol is preferably used as the solvent, for example, ethanol with sodium ethylate as the base. With the use of hydroxides or weaker bases, water or an aqueous solvent mixture can also be used.

The condensation is performed preferably at approximately ambient temperature so that neither heating nor cooling is required, i.e., approximately in the range of 10° to 40° C.

After distilling off the solvent, the reaction product of formula IV is advantageously mixed without purification with hydrochloric acid and cyclized. Hydrogen chloride is prefereably used in the form of aqueous hydrochloric acid, especially preferred in a concentration of 4 to 8M. Also the cyclization can be performed in the ambient temperature range without special temperature control measures.

The following examples illustrate the performance of the process according to the invention.

EXAMPLE 1

Dicyanoketene Dimethyl Thioacetal

To a sodium methylate solution of 2.3 g (0.1 mol) of sodium and 41 g of ethanol, 6.6 g (0.1 mol) of malononitrile (melted) was instilled under exclusion of moisture within 5 minutes at room temperature with stirring and then stirred for another 5 minutes at room temperature. The resultant suspension was cooled to 15° C. and, at this temperature, solutions of 7.6 g (0.1 mol) of carbon disulfide in 36 g of ethanol and 2.3 g (0.1 mol) of sodium in 41 g of ethanol were added within 60 minutes from two injection syringes operated synchronously. During the addition, a clear yellow-green solution formed, which was stirred for another 60 minutes. Then 26.5 g (0.21 mol) of dimethyl sulfate from a dropping funnel was added within 30 minutes with stirring. The temperature rose in this connection and was held at 20° C. by cooling. A yellow suspension resulted, which was stirred another 4 hours at 20° C. and then poured with stirring in 400 g of ice water. The aqueous ethanolic suspension was stirred for 2 hours more at room temperature for the decomposition of excess dimethyl sulfate, cooled to 5° C. and filtered. The filter cake was washed with a little water and dried at room temperature in a vacuum. There was a yield of 14.1 g of yellowish crystal with a content (HPLC) of 99.9 percent (83 percent of theory, relative to malononitrile.

The product had a melting point of 78° to 79.5° C. (Lit. 81° C.)

EXAMPLE 2

4-Amino-2-chloro-5-cyano-6-(methylthio)pyrimidine

A sodium methylate solution was produced from 0.23 g of sodium (10 mmol) and 25 ml of ethanol. 0.42 g of cyanamide (10 mmol) was dissolved in it and <then 1.70 g of dicyanoketene dimethyl thioacetal (10 mmol) was added. The yellowish suspension which formed was stirred 1 hour at 20° C. and then evaporated to dryness. A mixture of 20 ml of concentrated hydrochloric acid and 12 ml of water was added to the residue (1.98 g of yellow powder) at O° C. within 15 minutes. The resultant yellowish suspension was stirred another 20 hours at room temperature. The solid product was filtered off, washed with a little water, suspended in 60 ml of 10 percent sodium carbonate solution, again filtered off and washed with water. Finally the product was dried at 30° C./30 mbar. There was a yield of 1.95 g of yellowish power with a content (GC) of 96 percent (93 percent of theory). The product had a melting point of about 268° C.

What is claimed is:

1. Process for the production of 4-amino-2-chloro-5-cyano-6-(methylthio)pyrimidine of the formula:

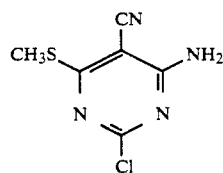

comprising reacting malononitrile with carbon disulfide in the presence of a strong base to obtain a dianion of dicyanodithioacetic acid of the formula:

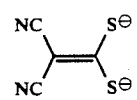

and then is methylating the dianion of dicyanodithioacetic acid of formula II with a methylating agent to obtain a dicyanoketene dimethyl thioacetal of the formula:

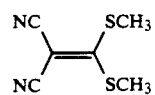

condensing the dicyanoketene dimethyl thioacetal of formula III with cyanamide in the presence of a base to obtain an anion of 2-cyano-3-cyanamino-3-methylthioacrylotirile of the formula:

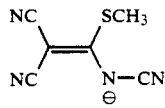

and then the anion of 2-cyano-3-cyanoamino-3-methylthio-acrylonitrile of formula IV is cyclized in the presence of hydrochloric acid to obtain the 4-amino-2-chloro-5-cyano-6-(methylthio)pyrimidine.

2. The process according to claim 1 wherein an alkali alcoholate is used as the base in the reaction step and in the condensation step.

3. The processing according to claim 2 wherein an alcohol is used as a solvent in the presence of the alkali alcoholate, the alcohol corresponding to the alcohol entity in the alkali alcoholate.

4. The process according to claim 3 wherein sodium ethylate is used as the alkali alcoholate.

5. The process according to claim 4 wherein, in the reaction of malononitrile with the carbon disulfide the malonic acid dinitrile is introduced with an equivalent of the base and the carbon disulfide is added synchronously with a second equivalent of the base.

6. The process according to claim 5 wherein dimethyl sulfate is used as the methylating agent.

7. The process according to claim 6 wherein the hydrochloric acid is used as aqueous hydrochloric acid.

8. The process according to claim 1 wherein, in the reaction of malononitrile with the carbon disulfide, the malononitrile is introduced with an equivalent of the base and the carbon disulfide is added synchronously with a second equivalent of the base.

9. The process according to claim 1 wherein dimethyl sulfate is used as the methylating agent.

10. The process according to claim 1 wherein the hydrochloric acid is used as aqueous hydrochloric acid.

* * * * *